United States Patent [19]

Lynch et al.

[11] 3,977,234

[45] Aug. 31, 1976

[54] MEANS FOR DETERMINING THE SAYBOLT VISCOSITY OF A HYDROCARBON STREAM FOR A DESIRED TEMPERATURE

[75] Inventors: Charles R. Lynch, Port Arthur, Tex.; Edward A. Copeland, Joliet, Ill.; William D. White, Nederland, Tex.

[73] Assignee: Texaco Inc., New York, N.Y.

[22] Filed: July 9, 1975

[21] Appl. No.: 594,473

[52] U.S. Cl. .................................. 73/53; 73/54; 235/151.3
[51] Int. Cl.² .................................. G01N 11/00
[58] Field of Search ............ 73/53, 54; 235/151.35, 235/151.3

[56] References Cited
UNITED STATES PATENTS 3,557,609   1/1971   Woodle ................................. 73/53
3,720,096   3/1973   Woodle ................................. 73/53

*Primary Examiner*—Herbert Goldstein
*Assistant Examiner*—Joseph W. Roskos
*Attorney, Agent, or Firm*—T. H. Whaley; C. G. Ries; Ronald G. Gillespie

[57] ABSTRACT

A measuring system provides a signal corresponding to the Saybolt viscosity of a hydrocarbon stream for a desired temperature. The signal is recorded by a recorder. The measuring system includes sensors sensing the temperature, the gravity and the kinematic viscosity of the hydrocarbon stream. A computing circuit provides the signal corresponding to the Saybolt viscosity in accordance with the signals from the sensors.

10 Claims, 2 Drawing Figures

MEANS FOR DETERMINING THE SAYBOLT VISCOSITY OF A HYDROCARBON STREAM FOR A DESIRED TEMPERATURE

BACKGROUND OF THE INVENTION

Field of the Invention

The system of the present invention is related to measuring systems in general and, more particularly, to a measuring system for a petroleum refining unit.

SUMMARY OF THE INVENTION

A system provides an output corresponding to the Saybolt viscosity of a hydrocarbon stream. The system includes a sensor sensing the specific gravity of the hydrocarbon stream and providing a corresponding signal. Another analyzer provides a signal corresponding to the viscosity of the hydrocarbon stream and a temperature sensor provides a signal corresponding to temperature of the hydrocarbon stream. A network receives the signals from the two analyzers and from the temperature sensor and provides the output corresponding to the Saybolt viscosity for desired temperature in accordance with the signals from the sensor and the analyzers.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustrative purposes only and are not to be construed as defining the limits of the invention.

DESCRIPTION OF THE INVENTION

Figure 1:
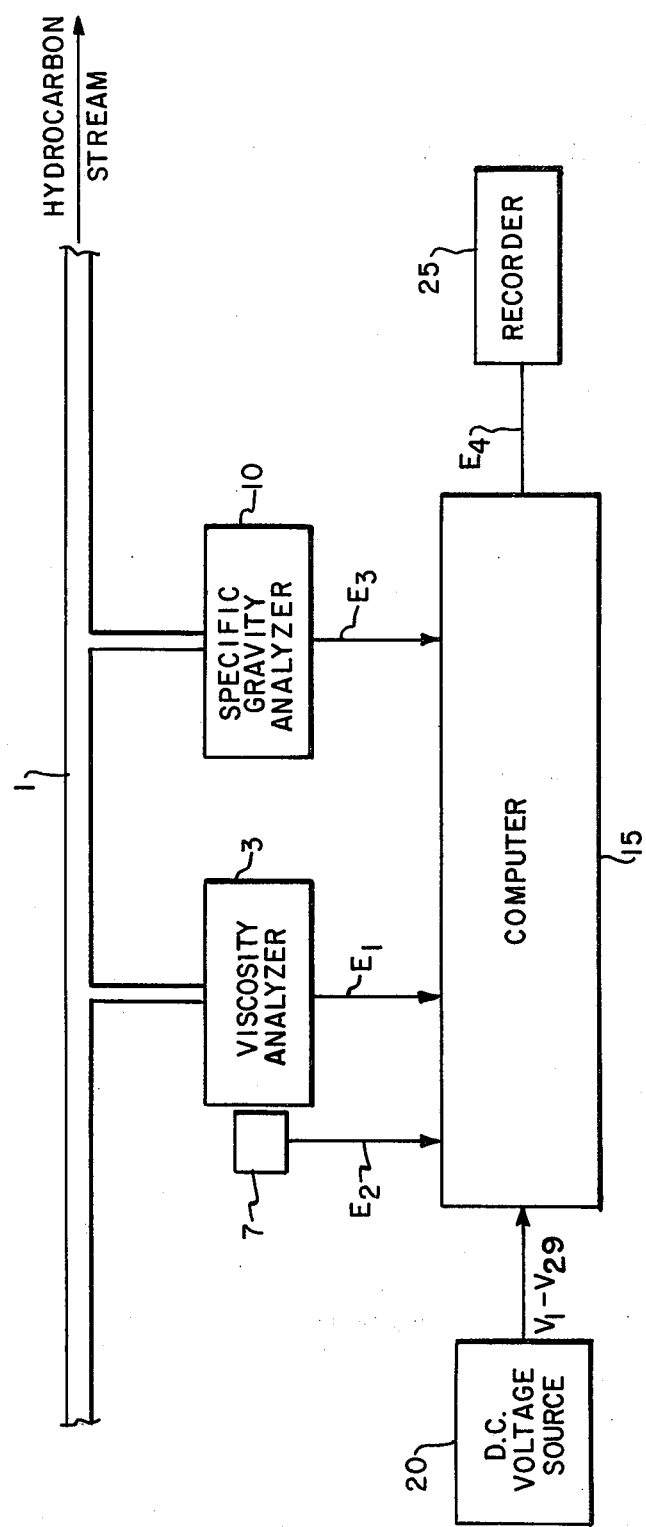
FIG. 1 is a simplified block diagram of apparatus, constructed in accordance with the present invention, for measuring and recording the Saybolt viscosity of a hydrocarbon stream for a desired temperature.

In the control of various hydrocarbon processing units, knowledge of the viscosity of a hydrocarbon stream at a particular or desired temperature may be important. For example, in the control of a crude oil distillation unit that is producing distillates for the manufacture of various grades of lubricating oil, viscosity specifications are generally established for each lube oil range distillate. Poor control of the distillate viscosity causes either a lower yield of the finished oils or extra processing costs. Referring to FIG. 1, there is shown apparatus for measuring and recording the Saybolt viscosity of oil in a hydrocarbon stream for a desired temperature. The hydrocarbon stream is passing through a line 1 where a viscosity analyzer 3 samples the hydrocarbon stream and provides a signal $E_1$ corresponding to the viscosity of the hydrocarbon stream in centipoise. The temperature transmitter 7 provides a signal $E_2$ corresponding to the temperature of the sampled hydrocarbon stream. A specific gravity analyzer 10 samples the hydrocarbon stream and provides a signal $E_3$ corresponding to the specific gravity of the hydrocarbon in line 1. Signals $E_1$ through $E_3$ are applied to a computer 15 which also receives voltages $V_1$ through $V_{29}$ from a DC voltage source 20. Computer 15 provides a signal $E_4$ corresponding to the Saybolt viscosity for a desired temperature in units of Saybolt Universal Seconds in accordance with equations hereinafter disclosed.

$$CSG = -K_1 + K_2(SG) - K_3(SG)^2 + K_4T - K_5T^2 - K_6(SG)T + K_7(SG)^3T + K_8(SG)^2T^2 \quad (1)$$

$$CAPI = \frac{K_9}{CSG} - K_{10} \quad (2)$$

$$SL = -K_{11} + K_{12}(CAPI) \quad (3)$$

$$VCST = \frac{(VCP)}{(SG)} \quad (4)$$

$$H = K_{13}\ln[\ln(VCST + K_{14})] \quad (5)$$

$$HA = H + (SL)(T_{spec} - T) \quad (6)$$

$$CSTA = e^{e^{(HA/K_{15})}} - K_{27} \quad (7)$$

$$SUS = K_{16} + K_{17}(T_{spec} - K_{18})\,K_{19}(CSTA) + \frac{K_{20} + K_{21}(CSTA)}{K_{22} + K_{23}(CSTA) + K_{24}(CSTA)2 + K_{25}(CSTA)3}\,K_{26} \quad (8)$$

where $CSG$ is the specific gravity of the hydrocarbon stream corrected to a temperature of 60°F, $SG$ is the sensed specific gravity of the hydrocarbon stream, $T$ is the temperature of the hydrocarbon stream, $CAPI$ is the API gravity of the hydrocarbon stream corrected to a temperature of 60°F, $SL$ is a slope factor, $VCST$ is the viscosity of the hydrocarbon stream in centistokes, $VCP$ is the sensed viscosity of the hydrocarbon in centipoise, $H$ is a modified Bell & Sharp H factor, $HA$ is the H value adjusted to a desired temperature, $T_{spec}$, at which the viscosity is to be determined, CSTA is the viscosity adjusted to the desired temperature, SUS is Saybolt Universal Seconds viscosity, and $K_1$ through $K_{27}$ are constants having the following preferred values: 0.11115, 1.17773, 0.087508, 0.001586, 0.00000064, 0.00181526, 0.000579, 0.00000062, 141.5, 131.5, 2.914, 0.0288, 377.8362, 0.6, 377.8362, 1.0, 0.000061, 100, 4.632, 1.0, 0.03264, 3930.2, 262.7, 23.97, 1.646, 10$^{-5}$ and 0.6, respectively.

Figure 2:
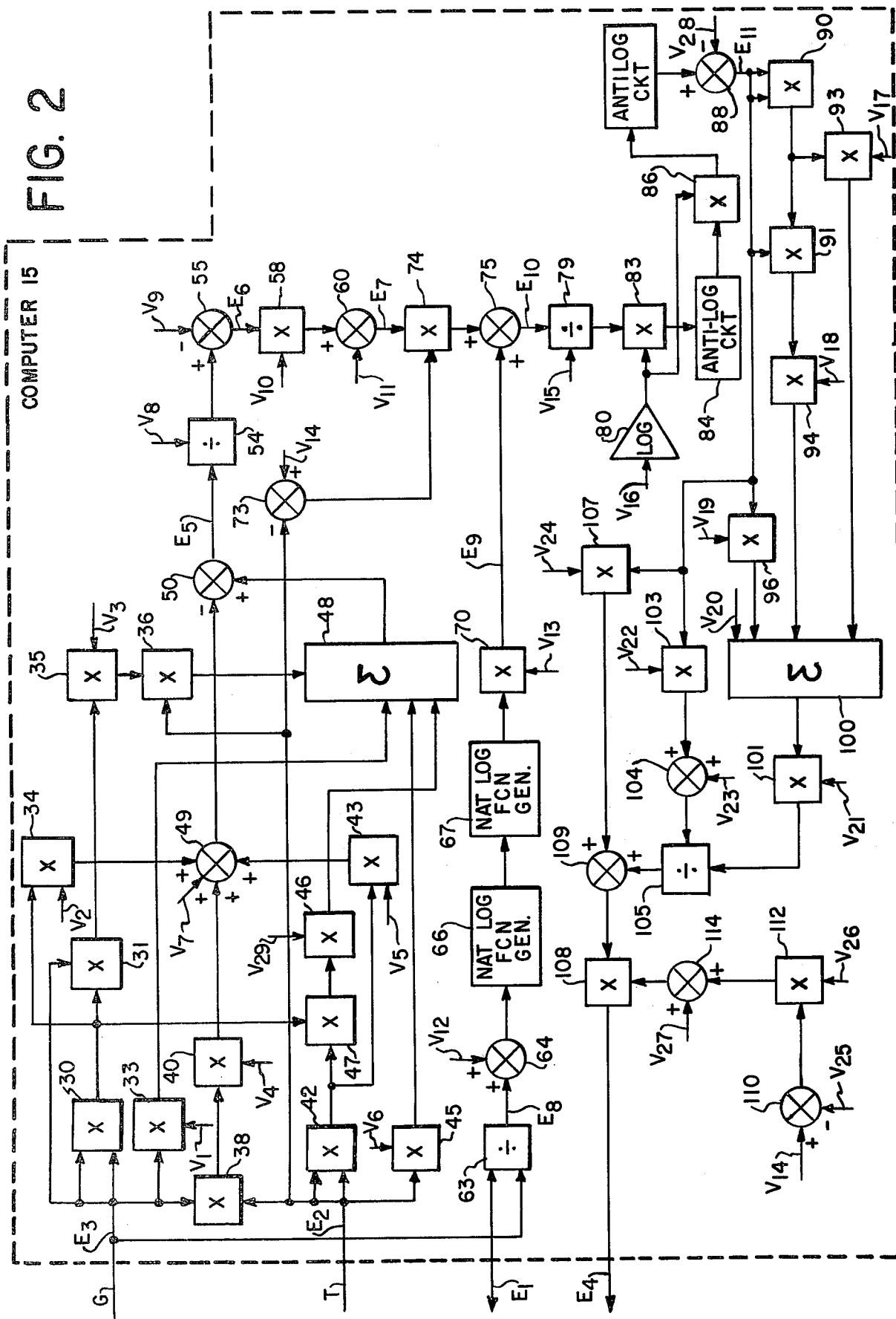
FIG. 2 is a detailed block diagram of the computer shown in FIG. 1.

Referring now to FIG. 2, there is shown computer 15 receiving signals $E_1$ through $E_3$ and providing signal $E_4$. It should be noted that the direct current voltages $V_1$ through $V_{29}$ from source 20 are not shown as entering computer 15 but are shown at the elements where they are utilized for convenience in reading FIG. 2. Signal $E_3$ is effectively squared by a multiplier 30 to provide a signal corresponding to the term $[SG]^2$. Another multiplier 31 multiplies the signal from multiplier 30 with $E_3$ to provide a signal corresponding to $[SG]^3$. A multiplier 33 multiplies signal $E_3$ with voltage $V_1$ to provide a signal corresponding to the term $K_2[SG]$ in equation 1. A multiplier 34 multiplies the signal from multiplier 30 with voltage $V_2$ to provide a signal corresponding to the term $K_3[SG]^2$. Another multiplier 35 multiplies the signal from multiplier 31 with voltage $V_3$ to provide a signal corresponding to the term $K_7[SG]^3$ in equation 1. Another multiplier 36 multiplies the signal from multiplier 35 with signal $E_2$ to provide a signal corresponding to the term $K_7SG3T$ in equation 1.

A multiplier 38 multiplies signal $E_2$ with signal $E_3$ to provide a signal corresponding to the term [SG]T. A multiplier 40 multiplies the signal from multiplier 38 with voltage $V_4$ to provide a signal corresponding to the term $K_6$[SG]T in equation 1.

Another multiplier 42 effectively squares signal $E_2$ to provide a signal corresponding to $T^2$. A multiplier 43 multiplies the signal from multiplier 42 with voltage $V_5$ to provide a signal corresponding to the term $K_5T^2$ in equation 1. A multiplier 45 multiplies signal $E_2$ with voltage $V_6$ to provide a signal corresponding to the term $K_4T$ in equation 1. A multiplier 47 multiplies the signals from multipliers 30, 42 to provide a signal corresponding to $[SG]^2T^2$ in equation 1. A multiplier 46 multiplies the signal from multiplier 47 by $V_{29}$ to provide a signal corresponding to the term $K_8(SG)^2T^2$ in equation 1. Summing means 48 in effect sums all the positive terms in equation 1. Summing means 48 sums the signals from multipliers 33, 35, 45 and 46 to provide a sum signal. Summing means 49 in effect sums all the negative terms in equation 1. Summing means 49 sums signals from multipliers 34, 40 and 43 with voltage $V_7$ which corresponds to the constant $K_1$, to provide a sum signal. Subtracting means 50 subtracts the signal provided by summing means 49 from the signals provided by the summing means 48 to provide a signal $E_5$ corresponding to the term CSG in equation 1.

A divider 54 divides voltage $V_8$ by signal $E_5$ to provide a signal corresponding to the term $K_9$/CSG. Subtracting means 55 subtracts voltage $V_9$, corresponding to the constant $K_{10}$, from the signal provided by divider 54 to provide a signal $E_6$ corresponding to CAPI in equation 2.

A multiplier 58 multiplies signal $E_6$ with voltage $V_{10}$ to provide a signal corresponding to the term $K_{12}$[CAPI] in equation 3. Subtracting means 60 subtracts voltage $V_{11}$ corresponding to the constant $K_{11}$, from the signal provided by multiplier 58 to provide a signal $E_7$ corresponding to the term SL.

A divider 63 divides signal $E_1$ with signal $E_3$ to provide a signal $E_8$ corresponding to the term VCST in equations 4 and 5.

Signal $E_8$ is summed with voltage $V_{12}$, corresponding to the constant $K_{14}$, to provide a signal corresponding to the term (VCST + $K_{14}$). A natural log function generator 66 provides a signal which is applied to another natural log function generator 67 which provides a signal corresponding to the term $\ln[\ln(VCST+K_{14})]$. A multiplier 70 multiplies the signal from function generator 67 with voltage $V_{13}$, corresponding to the constant $K_{13}$, to provide a signal $E_9$ corresponding to the term H in equations 5 and 6.

Subtracting means 73 subtracts signal $E_2$ from voltage $V_{14}$, corresponding to the desired temperature, to provide a signal corresponding to the term $[T_{spec}-T]$. A multiplier 74 multiplies the signal from subtracting means 73 with signal $E_7$ to provide a signal corresponding to the term $[SL][T_{spec}-T]$ in equation 6. Summing means 75 sums the signal from multiplier 74 with signal $E_9$ to provide a signal $E_{10}$ corresponding to the term HA in equations 6 and 7.

A divider 79 divides signal $E_{10}$ with a voltage $V_{15}$, corresponding to the constant $K_{15}$, to provide a signal corresponding to the term $[HA/K_{15}]$ in equation 7. Voltage $V_{16}$ corresponding to the mathematical constant $e$ is applied to a logarithmic amplifier 80 which provides a signal corresponding to $\log e$. A multiplier 83 multiplies the signal from amplifier 80 with the signal from divider 79 to provide a signal to an antilog circuit 84. The signal from antilog circuit 84 is multiplied with the signal from amplifier 80 by another multiplier 86 to provide a signal to an antilog circuit 87. Subtracting means 88 subtracts voltage $V_{28}$ from the signal from antilog circuit 87 to provide a signal $E_{11}$ corresponding to the term CSTA in equations 7 and 8. Voltage $V_{28}$ corresponds to the term $K_{27}$ in equation 7.

A multiplier 90 effectively squares signal $E_{11}$; another multiplier 91 multiplies the signal from multiplier 90 with signal $E_{11}$ to provide a signal corresponding to the term $(CSTA)^3$. A multiplier 93 multiplies the signal from multiplier 90 with voltage $V_{17}$, corresponding to the constant $K_{24}$, to provide a signal corresponding to $K_{24}$ $[CSTA]^2$ in equation 8. A multiplier 94 multiplies the signal from multiplier 91 with voltage $V_{18}$, corresponding to the constant $K_{25}$, to provide a signal corresponding to the term $K_{25}[CSTA]^3$. A multiplier 96 multiplies signal $E_{11}$ with voltage $V_{19}$, corresponding to the constant $K_{23}$, to provide a signal corresponding to the term $K_{23}$[CSTA].

Summing means 100 sums the signals from multipliers 93, 94 and 96 with voltage $V_{20}$, corresponding to the constant $K_{22}$, to provide a sum signal to a multiplier 101 where it is multiplied with voltage $V_{21}$ corresponding to the constant $K_{26}$. Multiplier 103 multiplies signal $E_{11}$ with voltage $V_{22}$, corresponding to the constant $K_{21}$, to provide a signal corresponding to the term $K_{21}$[CSTA]. Summing means 104 sums the signal provided by multiplier 103 with voltage $V_{23}$, corresponding to the constant $K_{20}$, to provide a signal corresponding to the term $[K_{20}+K_{21}(CSTA)]$.

A divider 105 divides the signal provided by the summing means 104 with the signal provided by multiplier 101. Multiplier 107 multiplies signal $E_{11}$ with voltage $V_{24}$, corresponding to the constant $K_{19}$, to provide a signal corresponding to the term $K_{19}$[CSTA]. Summing means 109 sums the signals from divider 105 and multiplier 107 to provide a sum signal.

Subtracting means 110 subtracts voltage $V_{25}$, corresponding to the constant $K_{18}$, from voltage $V_{14}$ to provide a signal corresponding to the term $(T_{spec}-T)$. A multiplier 112 multiplies the signal from subtracting means 110 with voltage $V_{26}$, corresponding to the constant $K_{17}$, to provide a signal corresponding to the term $K_{17}[T_{spec}-K_{18}]$. Summing means 114 sums the signal from multiplier 112 with voltage $V_{27}$ corresponding to the constant $K_{16}$, to provide a signal corresponding to the term $[K_{16}+K_{17}(T_{spec}-K_{18})]$. A multiplier 108 multiplies the signals from summing means 109 and 114 to provide signal $E_4$ which corresponds to the term SUS in equation 8.

The system of the invention as hereinbefore described determines the Saybolt viscosity of a hydrocarbon stream for a desired temperature on line and provides a recording thereof. In determining the Saybolt viscosity, the temperature, the specific gravity and the kinematic viscosity of the hydrocarbon stream are sensed.

What is claimed is:

1. A system for providing an output corresponding to the Saybolt viscosity of a hydrocarbon stream for a desired temperature, comprising means for sensing the specific gravity of the hydrocarbon stream and providing a signal SG corresponding thereto, means for sensing the temperature of the hydrocarbon stream and providing a signal T representative thereof, means for sensing the viscosity of the hydrocarbon stream and providing a corresponding signal VCP, means connected to the specific gravity sensing means and to the temperature sensing means for providing a signal corresponding to a specific gravity CSG corrected to a predetermined temperature in accordance with the T and SG signals, means connected to the CSG signal means for providing a signal CAPI corresponding to an API gravity corrected to the predetermined temperature in accordance with the CSG signal, means connected to CAPI signal means for providing a signal SL corresponding to a slope factor in accordance with the CAPI signal means connected to the viscosity sensing means and to the specific sensing means for providing a signal VCST corresponding to the viscosity of the hydrocarbon stream in centistokes in accordance with the SG and VCP signals, means connected to the VCST signal means for providing a signal H corresponding to an H factor in accordance with the VCST signal, means connected to the H signal means, to the SL signal means and to the temperature sensing means for providing a signal HA corresponding to an adjusted H factor, H being adjusted to the desired temperature, means connected to the HA signal means for providing a signal CSTA corresponding to the viscosity of the hydrocarbon stream adjusted to the desired temperature, and output network means connected to the CSTA signal means for providing a signal SUS as the output which corresponds to the Saybolt viscosity for the desired temperature in accordance with CSTA signal.

2. A system as described in claim 1 in which the CSG signal means provides CSG signal in accordance with the following equation:

$$CSG = -K_1 + K_2(SG) - K_3(SG)^2 + K_4T - K_5T^2 - K_6(SG)(T) + K_7(SG)^3(T) + K_8(SG)^2(T)^2.$$

where $K_1$ through $K_8$ are constants.

3. A system as described in claim 2 in which the CAPI signal means provides the CAPI signal in accordance with the following equation:

$$CAPI = (K_9/CSG) - K_{10},$$

where $K_9$ and $K_{10}$ are constants.

4. A system as described in claim 3 in which the SL signal means provides the SL signal in accordance with the following equation:

$$SL = -K_{11} + K_{12}(CAPI),$$

where $K_{11}$ and $K_{12}$ are constants.

5. A system as described in claim 4 in which the VCST signal means provides the VCST signal in accordance with the following equation:

$$VCST = VCP/SG.$$

6. A system as described in claim 5 in which the H signal means provides the H signal in accordance with the following equation:

$$H = K_{13} \ln[\ln(VCST + K_{14})],$$

where $K_{13}$ and $K_{14}$ are constants.

7. A system as described in claim 6 in which the HA signal means provides the HA signal in accordance with the following equation:

$$HA = H + (SL)(T_{spec} - T),$$

where $T_{spec}$ is the desired temperature.

8. A system as described in claim 7 in which the CSTA signal means provides the CSTA signal in accordance with the following equation:

$$CSTA = e^{e^{(HA/K_{15})}} - K_{27}$$

where $e$ is a mathematical constant and $K_{15}$ and $K_{27}$ are constants.

9. A system as described in claim 8 in which the output network means provides the SUS signal as the output in accordance with the following equation:

$$SUS = K_{16} + K_{17}(T_{spec} - K_{18})(K_{19}(CSTA) + [K_{20} + K_{21}(CSTA) \; / \; K_{22} + K_{23}(CSTA) + K_{24}(CSTA)^2 + K_{25}(CSTA)^3]K_{26}.$$

10. A system as described in claim 9 in which the predetermined temperature is 60°F and the constants $K_1$ through $K_{27}$ have preferred values of 0.11115, 1.1773, 0.087508, 0.001586, 0.00000064, 0.00181526, 0.000579, 0.00000062, 141.5, 131.5, 2.914, 0.0288, 377.8362, 0.6, 377.8362, 1.0, 0.000061, 100, 4.632, 1.0, 0.03264, 3930.2, 262.7, 23.97, 1.646, $10^{-5}$ and 0.6, respectively.

* * * * *

UNITED STATES PATENT OFFICE
CERTIFICATE OF CORRECTION

Patent No. 3,977,234   Dated August 31, 1976

Inventor(s) Charles R. Lynch et al.

It is certified that error appears in the above-identified patent and that said Letters Patent are hereby corrected as shown below:

Column 5, lines 38 and 39, should read $$\text{--CSG} = -K_1 + K_2(SG) - K_3(SG)^2 + K_4T - K_5T^2 - K_6(SG)(T) + K_7(SG)^3(T) + K_8(SG)^2(T)^2. \text{--}.$$

Signed and Sealed this

Thirty-first Day of May 1977

[SEAL]

Attest:

RUTH C. MASON
Attesting Officer

C. MARSHALL DANN
Commissioner of Patents and Trademarks